(12) United States Patent
Zhang et al.

(10) Patent No.: US 10,634,596 B2
(45) Date of Patent: Apr. 28, 2020

(54) VISUALIZED SUPERCRITICAL CARBON DIOXIDE FRACTURING PHYSICAL SIMULATION TEST METHOD

(71) Applicant: China University of Petroleum-Beijing, Beijing (CN)

(72) Inventors: Guangqing Zhang, Beijing (CN); Xuelin Zheng, Beijing (CN); Yuanyuan Wang, Beijing (CN); Cankun Lin, Beijing (CN)

(73) Assignee: China University of Petroleum-Beijing, Beijing (CN)

( * ) Notice: Subject to any disclaimer, the term of this patent is extended or adjusted under 35 U.S.C. 154(b) by 0 days.

(21) Appl. No.: 16/354,604

(22) Filed: Mar. 15, 2019

(65) Prior Publication Data
US 2020/0018671 A1 Jan. 16, 2020

(30) Foreign Application Priority Data
Jul. 11, 2018 (CN) .......................... 2018 1 0755321

(51) Int. Cl.
*G01N 3/10* (2006.01)
*G01N 33/24* (2006.01)
*H04N 5/225* (2006.01)

(52) U.S. Cl.
CPC .............. *G01N 3/10* (2013.01); *G01N 33/24* (2013.01); *H04N 5/2253* (2013.01);
(Continued)

(58) Field of Classification Search
CPC .. G01N 3/10; G01N 33/24; G01N 2203/0067; G01N 2203/0647;
(Continued)

(56) References Cited

U.S. PATENT DOCUMENTS 5,377,104 A    12/1994  Sorrells et al.
6,842,725 B1 *  1/2005  Sarda ..................... G01V 11/00
                                                        703/10
(Continued)

FOREIGN PATENT DOCUMENTS

CN    102373919 A    3/2012
CN    103244095 A    8/2013
(Continued)

OTHER PUBLICATIONS

First Chinese Office Action and Search Report for Application No. 201810755321.0 dated Jul. 29, 2019.
(Continued)

*Primary Examiner* — Alexander Gee
(74) *Attorney, Agent, or Firm* — Young Basile Hanlon & MacFarlane, P.C.

(57) ABSTRACT

The present invention relates to a visualized supercritical carbon dioxide fracturing physical simulation test method, comprising: preparing a rock sample, preparing a prefabricated fracture; curing the rock sample; fixing the cured rock sample in a confining pressure chamber, and applying a preset three-way confining pressure and pore pressure to the rock sample; turning on a high-speed camera, injecting supercritical carbon dioxide fracturing fluid to the central hole, and continuously recording a fluid injection pressure and test surface image information of the rock sample until the test is ended; observing a hydraulic fracture inside. Through this method, it is possible to obtain images in the whole process of initiation and extension of the artificial fracture during supercritical carbon dioxide fracturing, and distribution rules of parameters, such as stress, strain and pore pressure on the surfaces of the rock sample.

8 Claims, 6 Drawing Sheets

(52) U.S. Cl.
CPC ............... *G01N 2203/0044* (2013.01); *G01N 2203/0067* (2013.01); *G01N 2203/0647* (2013.01)

(58) Field of Classification Search
CPC .......... G01N 2223/506; H04N 5/2253; G01C 11/00; G07T 7/70; G07T 7/73
See application file for complete search history.

(56) References Cited

U.S. PATENT DOCUMENTS

| | | | | |
|---|---|---|---|---|
| 2003/0216898 | A1* | 11/2003 | Basquet | E21B 49/00 703/10 |
| 2008/0183451 | A1* | 7/2008 | Weng | E21B 43/26 703/10 |
| 2012/0223235 | A1* | 9/2012 | Maucec | G01N 33/24 250/362 |
| 2014/0327760 | A1* | 11/2014 | Kurz | H04N 5/332 348/135 |
| 2016/0176784 | A1* | 6/2016 | Okada | C01B 3/38 585/264 |
| 2016/0363691 | A1* | 12/2016 | Hu | G01V 1/345 |
| 2016/0370269 | A1* | 12/2016 | Hsueh | G01N 3/08 |
| 2017/0030819 | A1* | 2/2017 | McCarty | G01N 15/082 |
| 2017/0031048 | A1* | 2/2017 | Hilpert | E21B 49/00 |

FOREIGN PATENT DOCUMENTS

| | | |
|---|---|---|
| CN | 103266888 A | 8/2013 |
| CN | 103485759 A | 1/2014 |
| CN | 103712863 A | 4/2014 |
| CN | 104330310 A | 2/2015 |
| CN | 104458918 A | 3/2015 |
| WO | 2008/093264 A1 | 8/2008 |

OTHER PUBLICATIONS

Second Chinese Office Action for Application No. 201810755321.0 dated Sep. 10, 2019.
Third Chinese Office Action for Application No. 201810755321.0 dated Nov. 11, 2019.

* cited by examiner

VISUALIZED SUPERCRITICAL CARBON DIOXIDE FRACTURING PHYSICAL SIMULATION TEST METHOD

CROSS-REFERENCE TO RELATED APPLICATIONS

This application claims priority to Chinese Patent Application No. 201810755321.0, filed on Jul. 11, 2018, which is incorporated herein by reference in its entirety.

TECHNICAL FIELD

The present invention relates to the field of petroleum engineering rock mechanics, and particularly, to a visualized supercritical carbon dioxide fracturing physical simulation test method.

BACKGROUND ART

The amount of imported natural gases is growing with the demand on natural gases in China, and the dependence on foreign countries is correspondingly increasing, which seriously threatens the energy security in China. The shale gas resources are very rich in China, and the efficient development of the shale gas is of great significance for alleviating the contradiction between the energy supply and demand, adjusting the energy structure and ensuring the energy security. The amount of the shale gas resources in China is expected to reach $1.0 \times 1014$ m$^3$, which is twice of the amount of conventional natural gases. According to its recoverable resources and exploitation potential, the shale gas is expected to become a third important unconventional oil and gas resource following the coal bed gas and the tight sandstone gas.

Due to the characteristics of low porosity and low permeability of the shale gas reservoirs, reservoir fracturing and permeability increasing have to be carried out for the development of the shale gas. Currently, the United States mainly adopts the hydraulic fracturing technology to exploit the shale gas, but this technology consumes a lot of water resources and seriously pollutes the underground water; meanwhile, the content of clay in the shale in China is generally high, and the water-expandable characteristics of the shale will also affect the effect of reservoir transformation. In addition, China's proven shale gas reserves are mostly distributed in basins and mountainous areas where water resources are scarce, and the development of the shale gas in those areas also faces challenges in water resources.

When the temperature and pressure of carbon dioxide are above 31.10° C. and above 7.38 MPa, respectively, carbon dioxide will reach a supercritical state. Since the supercritical carbon dioxide has gas-like diffusivity as well as liquid density and solvency, while combining the characteristics such as low viscosity and low surface tension, it has excellent flow, penetration and transfer properties and can replace fresh water as a fracturing fluid. There are very few theoretical and experimental studies on the supercritical carbon dioxide fractured shale, especially corresponding test methods are absent for studying a process of artificial fracture initiation and extension during supercritical carbon dioxide fracturing, as well as information such as fracture length, fracture width and fracture extension speed of an artificial fracture during fracturing.

Therefore, by virtue of years of experiences and practices in related industries, the inventor proposes a visualized supercritical carbon dioxide fracturing physical simulation test method to overcome the defects of the prior art.

SUMMARY OF THE INVENTION

An objective of the present invention is to provide a visualized supercritical carbon dioxide fracturing physical simulation test method, through which it is possible to obtain images in the whole process of initiation and extension of the artificial fracture during supercritical carbon dioxide fracturing, and distribution rules of parameters, such as stress, strain and pore pressure on the surfaces of the rock sample.

The objective of the present invention is achieved by a visualized supercritical carbon dioxide fracturing physical simulation test method, comprising:

Step a: preparing a rock sample, drilling a central hole in the rock sample, and preparing a prefabricated fracture;

Step b: cladding and pasting an upper surface of the rock sample with an upper PVC film, cladding and pasting a lower surface of the rock sample with a lower PVC film, and placing the rock sample in an incubator for curing;

Step c: fixing the cured rock sample in a confining pressure chamber of a visualized two-dimensional hydraulic fracture simulation experimental device, and applying a preset three-way confining pressure and pore pressure to the rock sample;

Step d: turning on a high-speed camera at a top portion of the visualized two-dimensional hydraulic fracture simulation experimental device, injecting supercritical carbon dioxide fracturing fluid from a bottom to the central hole of the rock sample, and continuously recording a fluid injection pressure and test surface image information of the rock sample until the test is ended;

Step e: sequentially removing the fluid injection pressure, the pore pressure and the three-way confining pressure, taking out and sectioning the rock sample, and observing a hydraulic fracture inside the rock sample.

In a preferred embodiment of the present invention, in step a, the rock sample is a natural rock or an artificial rock.

In a preferred embodiment of the present invention, in step c, the visualized two-dimensional hydraulic fracture simulation experimental device comprises a confining pressure chamber, a pressurization device and a control portion; the confining pressure chamber has a rectangular cross section, and a top portion of the confining pressure chamber is hermetically provided with an upper cover which is dismountable and provided with a sealed transparent window; the confining pressure chamber is further provided with a through and sealable vent hole that can be communicated with a vacuum pump or a pore pressure pump;

The pressurization device comprises a lateral pressurization plate provided in the confining pressure chamber and capable of applying a horizontal pressure to the rock sample; the lateral pressurization plate is connected with a lateral pressurization hydraulic structure capable of driving the lateral pressurization plate to move horizontally and applying a horizontal pressure; one sidewall of the confining pressure chamber is set as a first sidewall, and the other sidewall adjacent to the first sidewall is set as a second sidewall; the lateral pressurization plate comprises a first lateral pressurization plate provided in parallel with the first sidewall, and a second lateral pressurization plate provided in parallel with the second sidewall; the lateral pressurization hydraulic structure comprises a first lateral pressurization hydraulic cylinder provided on an outer wall of the first sidewall and capable of driving the first lateral pressurization plate to move horizontally in a lengthwise direction of the second sidewall; the lateral pressurization hydraulic structure further comprises a second lateral pressurization hydraulic cylinder provided on an outer wall of the second sidewall and capable of driving the second lateral pressurization plate to move horizontally in a lengthwise direction of the first sidewall; both the first lateral pressurization hydraulic cylinder and the second lateral pressurization hydraulic cylinder are provided to be in communication with a confining pressure pump; the pressurization device further comprises a longitudinal pressurization plate hermetically provided at a bottom portion of the confining pressure chamber and capable of applying a vertical pressure to the rock sample; a bottom portion of the longitudinal pressurization plate is detachably connected with a longitudinal pressurization hydraulic cylinder capable of driving the longitudinal pressurization plate to move up and down and applying a vertical pressure; the longitudinal pressurization plate is provided with a plurality of fluid injection holes and a plurality of pressure measuring holes, each of the fluid injection holes is provided to be in communication with a fracturing fluid injection pump;

The control portion comprises a data collection unit and a control unit, wherein the data collection unit comprises the high-speed camera suspended above the upper cover and a pressure probe provided in each of the pressure measuring holes; the control unit is configured to receive image information and pressure information transmitted by the data collection unit, and capable of controlling work states of the fracturing fluid injection pump, the lateral pressurization hydraulic structure, and the longitudinal pressurization hydraulic cylinder.

In a preferred embodiment of the present invention, in step c, it is set that the vertical pressure applied to the rock sample by the longitudinal pressurization hydraulic cylinder is a Z-direction compressive stress, the horizontal pressure applied to the rock sample by the second lateral pressurization hydraulic cylinder is an X-direction horizontal compressive stress, the horizontal pressure applied to the rock sample by the first lateral pressurization hydraulic cylinder is a Y-direction horizontal compressive stress, and the prefabricated fracture is provided in the lengthwise direction of the first sidewall, wherein the X-direction horizontal compressive stress is greater than the Y-direction horizontal compressive stress; the Z-direction compressive stress, the X-direction horizontal compressive stress, and the Y-direction horizontal compressive stress constitute the three-way confining pressure of the rock sample.

In a preferred embodiment of the present invention, in step c, the vent hole in the confining pressure chamber is in communication with the pore pressure pump, and the pore pressure pump injects liquid into the confining pressure chamber, so that the rock sample is sufficiently saturated and reaches a preset pore pressure.

In a preferred embodiment of the present invention, in step d, the supercritical carbon dioxide fracturing fluid is injected into the confining pressure chamber via the fracturing fluid injection pump, with an injection rate of 5 ml/min to 25 ml/min.

In a preferred embodiment of the present invention, in step d, a temperature of the supercritical carbon dioxide fracturing fluid is above 32° C.

In a preferred embodiment of the present invention, in step d, when the fluid injection pressure of the supercritical carbon dioxide fracturing fluid is decreased to be 20% of a peak pressure, the fluid injection is stopped.

As can been from the above description, the visualized supercritical carbon dioxide fracturing physical simulation test method provided by the present invention has the following beneficial effects:

In the visualized supercritical carbon dioxide fracturing physical simulation test method provided by the present invention, the visualized two-dimensional hydraulic fracture simulation experimental device applies a nonuniform three-way confining pressure and a pore pressure to the rock sample, and simulates the environmental conditions of the actual three-way pressure and pore pressure experienced by the formation rocks; the high-speed camera can record the whole process of initiation and extension of the fracture of the rock sample during the supercritical carbon dioxide fracturing through a transparent window, and obtain distribution rules of parameters, such as stress and strain, on the rock sample during the supercritical carbon dioxide fracturing through the DIC technology and pressure monitoring. The visualized supercritical carbon dioxide fracturing physical simulation test method provided by the present invention is easily operable and strongly practical, and can provide more bases for the hydraulic fracturing design for the oil fields and research institutions.

BRIEF DESCRIPTION OF THE DRAWINGS

The following drawings are only intended to schematically illustrate and explain the present invention, rather than limiting the scope of the present invention. In which.

In which,

100: visualized two-dimensional hydraulic fracture simulation experimental device;

1: upper cover; 2: glass plate; 3: confining pressure chamber; 4: longitudinal pressurization plate; 5: first lateral pressurization plate; 6: testing machine rigid frame; 7: longitudinal hydraulic shaft; 71: groove structure; 8: longitudinal hydraulic cylinder barrel; 9: hydraulic cylinder base; 10: first connection rod; 11: first fixing nut; 12: first lateral hydraulic cylinder barrel; 13: first lateral end cover; 14: first lateral plug; 15: first lateral piston; 16: first fixing plate; 17: first lateral pressurization rod; 18: first pressure ring; 19: camera support; 20: high-speed camera; 21: rock sample; 22: upper PVC film; I: fluid injection port; II: fluid drainage port.

DETAILED DESCRIPTION OF THE PREFERRED EMBODIMENTS

In order that the technical features, objectives, and effects of the present invention can be more clearly understood, the embodiments of the present invention will be described with reference to the drawings.

The present invention provides a visualized supercritical carbon dioxide fracturing physical simulation test method, comprising:

Step a: preparing a rock sample 21, drilling a central hole in the rock sample 21, and preparing a prefabricated fracture;

Specifically, the rock sample 21 may be a natural rock or an artificial rock. The natural rock may be shale, marble, granite, etc., and the material of the artificial rock may be a transparent acrylic material.

When being prepared, the prefabricated fracture is located on the central hole.

In order to meet a data collection by a DIC device, according to the DIC technical requirement, surfaces of the rock sample 21 to be tested (an upper surface and a lower surface of the rock sample 21) are uniformly sprayed with a matt white paint, and then placed in a cool and ventilated place to be dried; next, matte black speckles are uniformly sprayed on the matt white paint and then dried; finally, speckles are formed on the surfaces to be tested.

Figure 7:
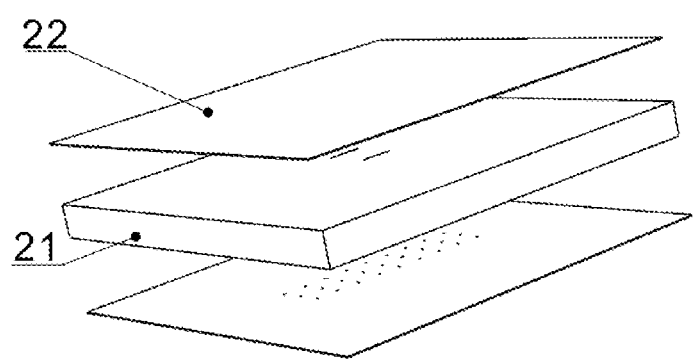
FIG. 7 is a schematic view of sealing of a rock sample of the present invention.

Step b: as shown in FIG. 7, cladding and pasting an upper surface of the rock sample 21 with an upper PVC film 22, cladding and pasting a lower surface of the rock sample with a lower PVC film that is provided with a plurality of film through-holes, and placing the rock sample 21 in an incubator for curing;

The upper PVC film 22 and the lower PVC film are pasted to the upper surface and the lower surface of the rock sample 21 by transparent resin glue, respectively; the rock sample 21 is sealed between the upper cover 1 and the longitudinal pressurization plate 4 during the test.

Step c: fixing the cured rock sample 21 in a confining pressure chamber 3 of a visualized two-dimensional hydraulic fracture simulation experimental device 100, and applying a preset three-way confining pressure and pore pressure to the rock sample 21.

Specifically, as shown in FIGS. 1 to 6, the visualized two-dimensional hydraulic fracture simulation experimental device 100 comprises the confining pressure chamber 3, a pressurization device, and a control portion.

As shown in FIGS. 1 to 4, the confining pressure chamber 3 is built on a testing machine rigid frame 6; the confining pressure chamber 3 has a rectangular cross section, and a top portion of the confining pressure chamber is hermetically provided with an upper cover 1 which is provided with a sealed transparent window; in this embodiment, a window through-hole is opened at a center of the upper cover 1, and a glass plate 2 is sealed and fixed below the window through-hole to constitute the aforementioned transparent window, wherein the glass plate 2 is a high-strength glass plate. The confining pressure chamber 3 is further provided with a through and sealable vent hole that can be communicated with a vacuum pump or a pore pressure pump; in this embodiment, the vent hole is provided with a valve switch having an outlet that can be opened and in sealed connection with the vacuum pump or the pore pressure pump. When the vent hole is opened, it is used for the confining pressure chamber to vent outward; when the vent hole is in communication with the vacuum pump, the vacuum pump vacuumizes the confining pressure chamber 3; and when the vent hole is in communication with the pore pressure pump, the pore pressure pump injects liquid into the confining pressure chamber 3, so that the rock sample 21 is sufficiently saturated and reaches a preset pore pressure, thereby hydraulically fracturing the rock sample 21 under the pore pressure condition.

The pressurization device comprises a lateral pressurization plate provided in the confining pressure chamber 3 and capable of applying a horizontal pressure to the rock sample 21; the lateral pressurization plate is connected with a lateral pressurization hydraulic structure capable of driving the lateral pressurization plate to move horizontally and applying a horizontal pressure; one sidewall of the confining pressure chamber 3 is set as a first sidewall, and the other sidewall adjacent to the first sidewall is set as a second sidewall; the lateral pressurization plate comprises a first lateral pressurization plate 5 provided in parallel with the first sidewall, and a second lateral pressurization plate provided in parallel with the second sidewall; the lateral pressurization hydraulic structure comprises a first lateral pressurization hydraulic cylinder provided on an outer wall of the first sidewall and capable of driving the first lateral pressurization plate 5 to move horizontally in a lengthwise direction of the second sidewall; the lateral pressurization hydraulic structure further comprises a second lateral pressurization hydraulic cylinder provided on an outer wall of the second sidewall and capable of driving the second lateral pressurization plate to move horizontally in a lengthwise direction of the first sidewall; both the first lateral pressurization hydraulic cylinder and the second lateral pressurization hydraulic cylinder are provided to be in communication with a confining pressure pump.

Figure 1:
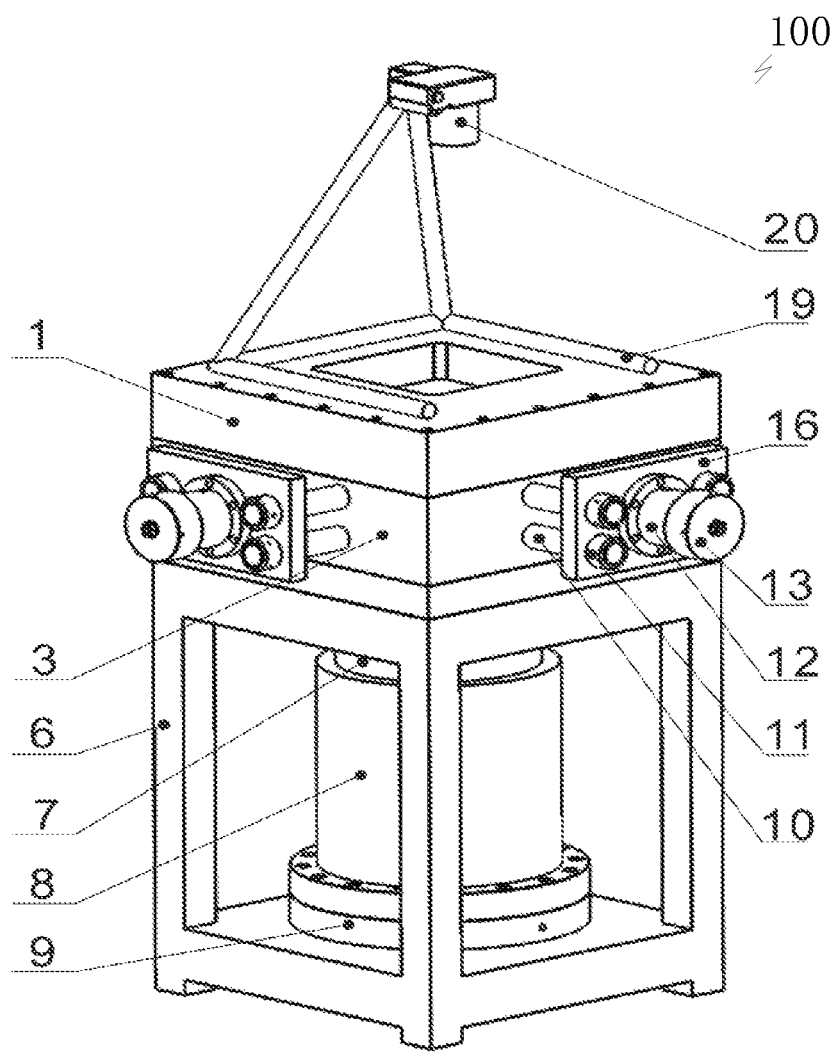
FIG. 1 is an overall schematic view of a visualized two-dimensional hydraulic fracture simulation experimental device of the present invention.
Figure 2:
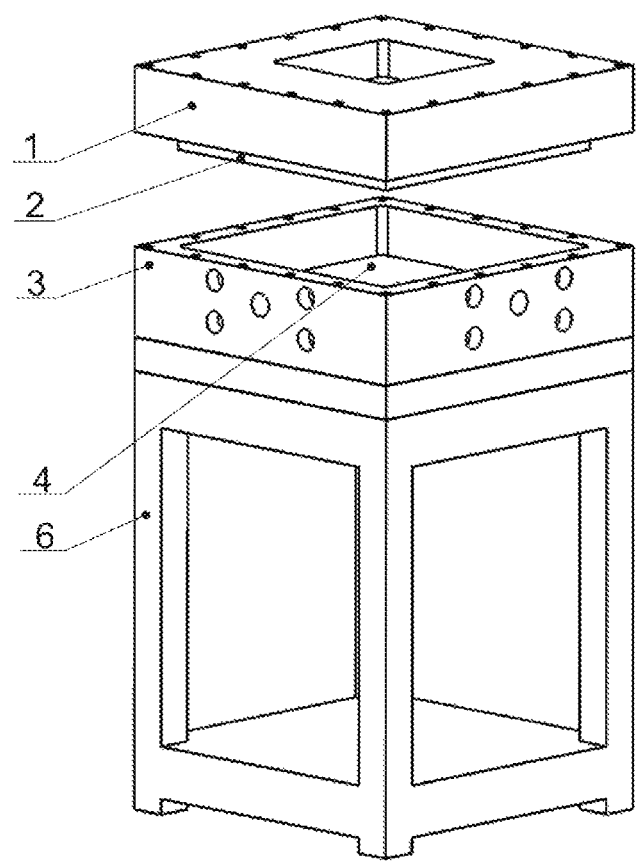
FIG. 2 is a schematic view of a confining pressure chamber and a testing machine rigid frame of the present invention.
Figure 3:
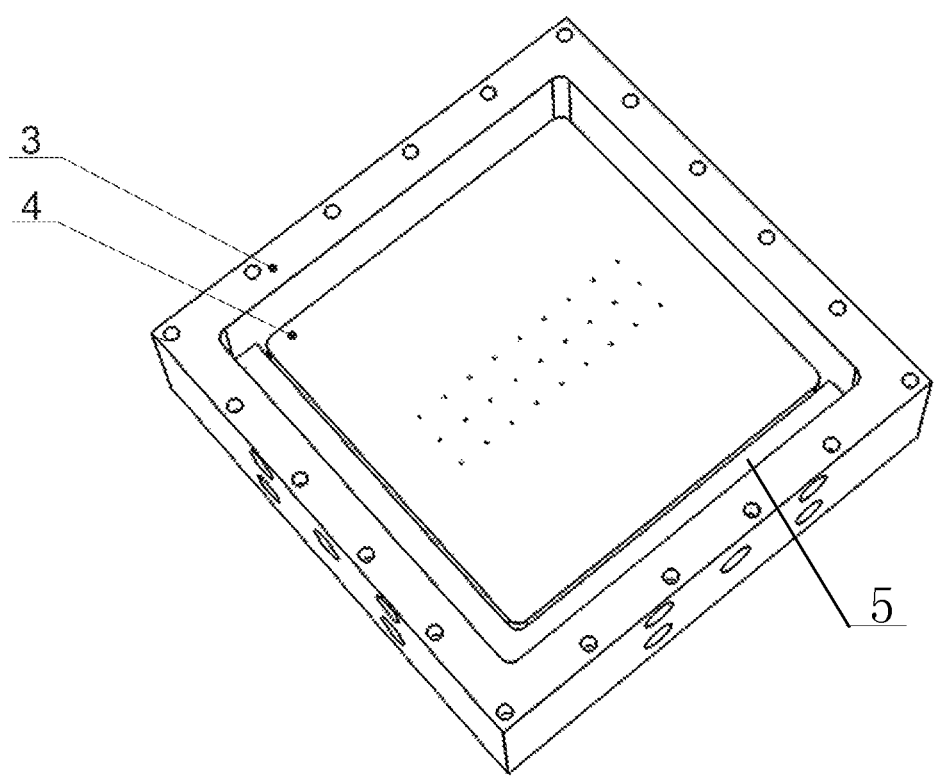
FIG. 3 is a schematic diagram of an internal layout of a confining pressure chamber of the present invention.
Figure 4:
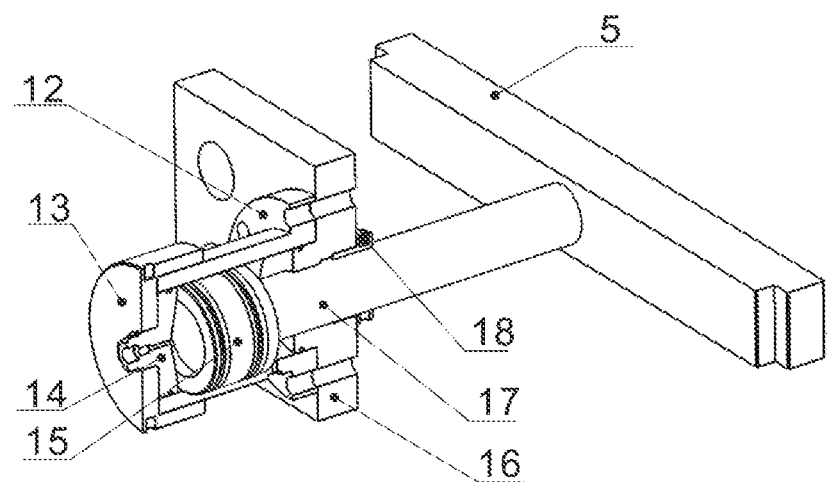
FIG. 4 is a schematic view of a structure at a first laterally pressurization hydraulic cylinder of the present invention.

In this embodiment, as shown in FIGS. 1 and 4, the first lateral pressurization hydraulic cylinder comprises a sealable first lateral hydraulic cylinder barrel 12 in which a first lateral piston 15 is hermetically provided and slidable; one end of the first lateral piston 15 is fixedly connected with a first lateral pressurization rod 17; one end of the first lateral pressurization rod 17 is sealed to pass through the first lateral hydraulic cylinder barrel 12 and then sealed to pass through the first sidewall, and the other end of the first lateral pressurization rod 17 is fixedly connected with the first lateral pressurization plate 5; the second lateral pressurization hydraulic cylinder and the first lateral pressurization hydraulic cylinder adopt the same structure. One end of the first lateral hydraulic cylinder barrel 12 is fixedly connected with a first fixing plate 16 that is fixedly connected with the first sidewall; the first fixing pressurization rod 16 is provided with a first lateral pressurization rod through-hole, through which the first lateral pressurization rod 17 is sealed to pass; in order to ensure the sealability, a first pressure ring 18 that is sealable to sleeve the first lateral pressurization rod 17 is hermetically provided at the first lateral pressurization rod through-hole; a first lateral plug 14 is sealed and sleeved in the other end of the first lateral hydraulic cylinder barrel 12, and a first lateral end cover 13 is sealed to sleeve the other end of the first lateral hydraulic cylinder barrel 12; in this embodiment, the first lateral plug 14 and the first lateral end cover 13 are provided with a hydraulic oil interface, through which the first lateral pressurization hydraulic cylinder is in communication with the confining pressure pump; one end of the second lateral hydraulic cylinder barrel is fixedly connected with the second fixing plate that is fixedly connected with the second sidewall; the second fixing plate is provided with a second pressurization rod through-hole, through which the second pressurization rod is sealed to pass.

As shown in FIG. 1, the first sidewall is provided with a plurality of first connection rods 10 extending horizontally outward, and the first fixing plate 16 is provided with first connection through-holes corresponding to the respective first connection rods 10 that pass through the first connection through-holes so as to be fixedly connected with first fixing nuts 11.

The second sidewall is provided with a plurality of second connection rods extending horizontally outward, and the second fixing plate is provided with second connection through-holes corresponding to the respective second connection rods that pass through the second connection through-holes so as to be fixedly connected with second fixing nuts.

The pressurization device further comprises a longitudinal pressurization plate 4 hermetically provided at a bottom portion of the confining pressure chamber 3 and capable of applying a vertical pressure to the rock sample 21; a bottom portion of the longitudinal pressurization plate 4 is detachably connected with a longitudinal pressurization hydraulic cylinder capable of driving the longitudinal pressurization plate to move up and down and applying a vertical pressure; the longitudinal pressurization plate 4 is provided with a plurality of fluid injection holes and a plurality of pressure measuring holes, each of the fluid injection holes is provided to be in communication with a fracturing fluid injection pump, and the plurality of fluid injection holes and the plurality of pressure measuring holes are corresponding to the plurality of film through-holes on the lower PVC film.

Figure 5:
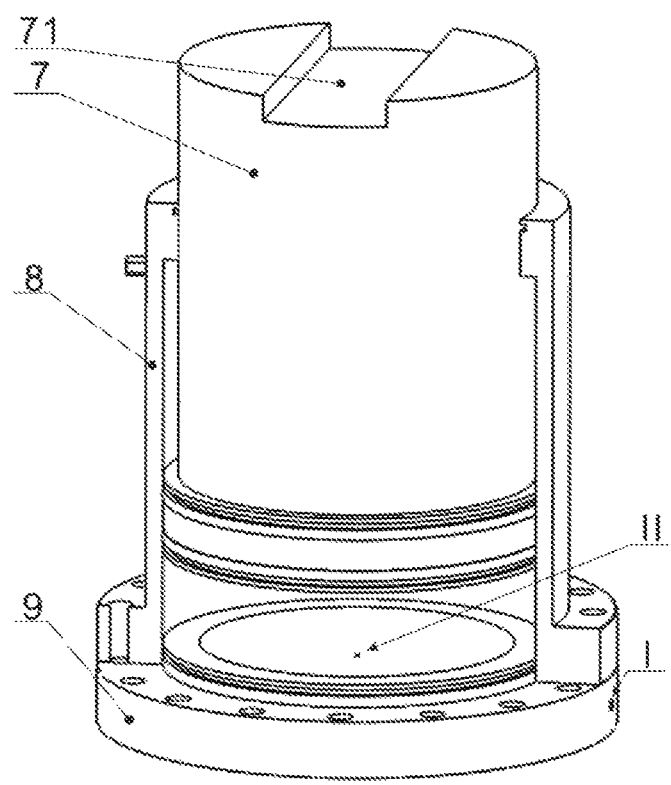
FIG. 5 is a schematic view of a structure at a longitudinally pressurization hydraulic cylinder of the present invention.

As shown in FIGS. 1 and 5, the longitudinal pressurization hydraulic cylinder is provided to be in communication with the confining pressure pump; the longitudinal pressurization hydraulic cylinder comprises a longitudinal hydraulic cylinder barrel 8 in which a longitudinal piston is hermetically provided and slidable; an upper gas chamber is formed above the longitudinal piston, and a lower fluid chamber is formed below the longitudinal piston; a gas hole is provided at a top portion of the longitudinal hydraulic cylinder barrel 8, and a fluid injection port and a fluid drainage port are provided at a bottom portion of the longitudinal hydraulic cylinder barrel 8; the lower fluid chamber receives oil, the longitudinal piston moves upward, and the upper gas chamber exhaust gas; the lower fluid chamber drains oil, the longitudinal piston moves downward, and the upper gas chamber takes gas in. The longitudinal piston is provided with a longitudinal hydraulic shaft 7 extending upward, and the other end of the longitudinal hydraulic shaft 7 is sealed to pass through a top end of the longitudinal hydraulic cylinder barrel 8 and then detachably connected with the longitudinal pressurization plate. In this embodiment, the top end of the longitudinal hydraulic cylinder barrel 8 is provided with a seal ring for sealing between the longitudinal hydraulic shaft 7 and the longitudinal hydraulic cylinder barrel 8. In this embodiment, the other end of the longitudinal hydraulic shaft 7 is provided with a groove structure 71 that reserves space for a connection line of the fluid injection hole and a pressure probe in the pressure measuring hole. Under the hydraulic effect, the longitudinal hydraulic shaft 7 drives the longitudinal pressurization plate pressure to rise and fall, and when the longitudinal pressurization plate falls to a limited lowest position of the confining pressure chamber 3, the longitudinal hydraulic shaft 7 is separated from the longitudinal pressurization plate.

In this embodiment, a hydraulic cylinder base 9 is detachably sealed at a bottom end of the longitudinal hydraulic cylinder barrel 8, and provided with a fluid injection port I and a fluid drainage port II. The longitudinal pressurization hydraulic cylinder is in communication with the confining pressure pump via the fluid injection port I and the fluid drainage port II. In this embodiment, the hydraulic cylinder base 9 is sealed from the bottom end of the longitudinal hydraulic cylinder barrel 8 via the seal ring.

It is set that the vertical pressure applied to the rock sample by the longitudinal pressurization hydraulic cylinder is a Z-direction compressive stress, the horizontal pressure applied to the rock sample by the second lateral pressurization hydraulic cylinder is an X-direction horizontal compressive stress, the horizontal pressure applied to the rock sample by the first lateral pressurization hydraulic cylinder is a Y-direction horizontal compressive stress, and the prefabricated fracture is provided in the lengthwise direction of the first sidewall, wherein the X-direction horizontal compressive stress is greater than the Y-direction horizontal compressive stress, and the Z-direction compressive stress, the X-direction horizontal compressive stress, and the Y-direction horizontal compressive stress constitute the three-way confining pressure of the rock sample.

Figure 6:
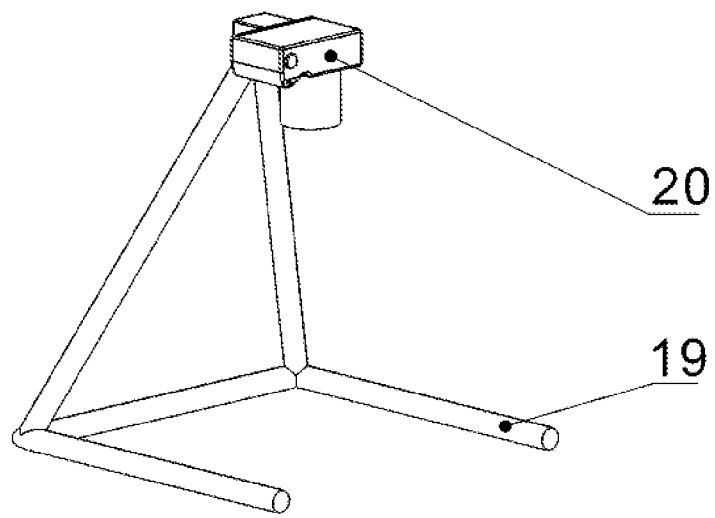
FIG. 6 is a schematic view of structures of a camera support and a high-speed camera of the present invention.

The control portion comprises a data collection unit and a control unit, wherein the data collection unit comprises the high-speed camera suspended above the upper cover and a pressure probe provided in each of the pressure measuring holes; as shown in FIG. 6, the upper cover 1 is provided with a camera support 19 on which the aforementioned high-speed camera 20 is mounted; the high-speed camera 20 can intuitively monitor the entire process of initiation and extension of a two-dimensional hydraulic fracture, and transmit a fracture image of the upper surface of the rock sample 21 to the control portion, so as to obtain, through a DIC method (optical method), a fracture length, a fracture width, an extension speed of the hydraulic fracture, and data such as the stress-strain field and the pore pressure field around the fracture. The control unit is configured to receive image information and pressure information transmitted by the data collection unit, and capable of controlling work states of the fracturing fluid injection pump, the lateral pressurization hydraulic structure, and the longitudinal pressurization hydraulic cylinder.

Step d: turning on the high-speed camera 20 at the top portion of the visualized two-dimensional hydraulic fracture simulation experimental device, injecting supercritical carbon dioxide fracturing fluid from the bottom to the central hole of the rock sample, and continuously recording a fluid injection pressure and test surface image information of the rock sample until the test is ended.

Specifically, in a particular embodiment of the present invention, the supercritical carbon dioxide fracturing fluid is injected into the confining pressure chamber via the fracturing fluid injection pump, with an injection rate of 5 ml/min to 25 ml/min and a temperature above 32° C.

When the fluid injection pressure of the supercritical carbon dioxide fracturing fluid is decreased to be 20% of a peak pressure, the fluid injection is stopped.

Step e: sequentially removing the fluid injection pressure, the pore pressure and the three-way confining pressure, taking out and sectioning the rock sample, and observing a hydraulic fracture inside the rock sample.

Embodiment

Step a: using a wire cutting device to cut an obtained natural marble material into test pieces each having a length of 500 mm, a width of 500 mm and a thickness of 5 mm, then using a drilling machine to drill a central hole having a diameter of 20 mm at a middle portion of a rock sample 21 from an upper surface of the rock sample 21 to a lower surface thereof, and finally using a wire-cutting saw to cut two prefabricated fractures each having a thickness of 2 mm and a length of 10 mm from a center of the central hole in the rock sample 21.

The upper surface and the lower surface of the rock sample 21 are uniformly sprayed with a matt white paint, and then placed in a cool and ventilated place to be dried; after the matt white paint is completely dried, matte black speckles are uniformly sprayed on the matt white paint and then dried; and finally, speckles are formed on the upper surface and the lower surface of the rock sample 21.

Step b: pasting an upper PVC film 22 and a lower PVC film which meet the experimental requirements on the upper surface and the lower surface of the rock sample 21 by transparent resin glue, respectively, thereby preventing liquid from leaking along the upper surface and the lower surface of the rock sample 21. The filmed rock sample 21 is placed in an incubator for curing, with a curing temperature of 55° C., and a curing time of 48 h.

Step c: placing the sealed rock sample 21 on the longitudinal pressurization plate 4, wherein the film through-holes in the lower PVC film on the lower surface of the rock sample 21 need to be one-to-one aligned with the fluid injection holes and the pressure measuring holes on the longitudinal pressurization plate 4, in order for the liquid injection and pore pressure measurement. Next, placing the upper cover 1 on the confining pressure chamber 3, fixing the upper cover 1 on the confining pressure chamber 3 by bolts, placing the camera support 19 and the high-speed camera 20 on the upper cover 1 so that a camera lens directly faces a central position of the transparent window of the upper cover 1, connecting the fluid injection holes in the longitudinal pressurization plate 4 to the fluid injection line, providing a pressure probe in the pressure measuring hole, and connecting a data transmission line between the high-speed camera 20 and the pressure probe to the control portion (data collection computer).

When the three-way confining pressure is applied to the rock sample 21, the valve switch at the vent hole of the confining pressure chamber 3 is opened to turn on the confining pressure pump to inject oil into the first lateral pressurization hydraulic cylinder, the second lateral pressurization hydraulic cylinder and the longitudinal pressurization hydraulic cylinder, respectively; the longitudinal hydraulic shaft 7 pushes the longitudinal pressurization plate 4 upward, so as to push the rock sample 21 toward the upper cover 1; the first lateral pressurization rod 17 pushes the first lateral pressurization plate 5 inward to press the rock sample 21; the second lateral pressurization rod pushes the second lateral pressurization plate inward to press the rock sample 21; and the confining pressure pump is turned off when the longitudinal pressurization plate 4, the glass plate 2 at the bottom portion of the upper cover 1, the first lateral pressurization plate 5 and the second lateral pressurization plate tightly press the rock sample 21.

The longitudinal pressurization plate 4 and the upper cover 1 apply a Z-direction compressive stress to the rock sample 21, the first lateral pressurization plate 5 applies a Y-direction horizontal compressive stress, the second lateral pressurization plate applies an X-direction horizontal compressive stress to the rock sample 21, the prefabricated fracture is provided in the lengthwise direction (X-direction) of the first sidewall, the X-direction horizontal compressive stress is greater than the Y-direction horizontal compressive stress, and the values of the X-direction horizontal compressive stress, the Y-direction horizontal compressive stress and the Z-direction compressive stress are 7 MPa, 5 MPa, 3 MPa, respectively, but the magnitude of the three-way confining pressure in the present invention is not limited thereto.

Next, the valve switch at the vent hole of the confining pressure chamber 3 is communicated with the vacuum pump, and the vacuum pump is turned on to vacuumize the rock sample 21 in the confining pressure chamber 3; next, the confining pressure pump is turned on to apply a confining pressure to the rock sample 21, and when a preset confining pressure is reached, the fluid injection is stopped, and the three-way confining pressure is maintained.

The valve switch at the vent hole of the confining pressure chamber 3 is communicated with the pore pressure pump, and the pore pressure pump is turned on to inject fluid into the confining pressure chamber 3; when the rock sample 21 is sufficiently saturated and reaches a preset pore pressure, the preset pore pressure is maintained. In this embodiment, the pore pressure applied to the rock sample 21 is 2 MPa, but the pore pressure in the present invention is not limited thereto.

Step d: turning on the high-speed camera, turning on the fracturing fluid injection pump, injecting a supercritical carbon dioxide fracturing fluid with a temperature of 35° C. into the central hole in the rock sample 21 via the fluid injection hole of the longitudinal pressurization plate 4 in a preset fluid injection speed, with a fluid injection displacement of 5 ml/min, recording experimental data until the fluid injection pressure of the rock sample 21 is decreased to be 20% of the fracture pressure.

Step e: after the rock sample 21 is fully fractured, the data collection (collection of the fracture image and the pore pressure) is stopped, and the fracturing fluid injection pump is turned off to decrease the injection pressure to be zero; the pore pressure pump is turned on, and the pore pressure applied to the rock sample 21 is cancelled; the first lateral pressurization hydraulic cylinder, the second lateral pressurization hydraulic cylinder and the longitudinal pressurization hydraulic cylinder drain the oil, the longitudinal pressurization plate 4 moves downward, the first lateral pressurization plate 5 and the second lateral pressurization plate move outward, and the glass plate 2 of the bottom portion 1 of the upper cover 1, the first lateral pressurization plate 5 and the second lateral pressurization plate are separated from the rock sample 21; next, the high-speed camera 20 and the camera support 19 are removed from the upper cover 1, the bolts of the connection upper cover 1 and the confining pressure chamber 3 are dismounted, and the upper cover 1 is lifted away with a lifting device; finally, the rock sample 21 is dismounted from the confining pressure chamber 3, and the rock sample 21 is sectioned to observe the hydraulic fracture inside the rock sample 21, thereby completing the entire experiment procedure.

As can been from the above description, the visualized supercritical carbon dioxide fracturing physical simulation test method provided by the present invention has the following beneficial effects:

In the visualized supercritical carbon dioxide fracturing physical simulation test method provided by the present invention, the visualized two-dimensional hydraulic fracture simulation experimental device 100 applies a nonuniform three-way confining pressure and a pore pressure to the rock sample, and simulates the environmental conditions of the actual three-way pressure and pore pressure experienced by the formation rocks; the high-speed camera can record the whole process of initiation and extension of the fracture of the rock sample during the supercritical carbon dioxide fracturing through a transparent window, and obtain distribution rules of parameters, such as stress and strain, on the rock sample during the supercritical carbon dioxide fracturing through the DIC technology and pressure monitoring. The visualized supercritical carbon dioxide fracturing physical simulation test method provided by the present invention is easily operable and strongly practical, and can provide more bases for the hydraulic fracturing design for the oil fields and research institutions.

The above descriptions are just schematic particular embodiments of the present invention, rather than limitations to the scope of the present invention. Any equivalent change or amendment, made by a person skilled in the art without deviating from the conception and principle of the present invention shall fall within the claimed scope of the present invention.

The invention claimed is:

1. A visualized supercritical carbon dioxide fracturing physical simulation test method, comprising:
    step a: preparing a rock sample, drilling a central hole in the rock sample, and preparing a prefabricated fracture;
    step b: cladding and pasting an upper surface of the rock sample with an upper PVC film, cladding and pasting a lower surface of the rock sample with a lower PVC film, and placing the rock sample in an incubator for curing;
    step c: fixing the cured rock sample in a confining pressure chamber of a visualized two-dimensional hydraulic fracture simulation experimental device, and applying a preset three-way confining pressure and pore pressure to the rock sample;
    step d: turning on a high-speed camera at a top portion of the visualized two-dimensional hydraulic fracture simulation experimental device, injecting supercritical carbon dioxide fracturing fluid from a bottom to the central hole of the rock sample, and continuously recording a fluid injection pressure and test surface image information of the rock sample until the test is ended; and
    step e: sequentially removing the fluid injection pressure, the pore pressure and the three-way confining pressure, taking out and sectioning the rock sample, and observing a hydraulic fracture inside the rock sample.

2. The visualized supercritical carbon dioxide fracturing physical simulation test method according to claim 1, wherein in step a, the rock sample is a natural rock or an artificial rock.

3. The visualized supercritical carbon dioxide fracturing physical simulation test method according to claim 1, wherein in step c, the visualized two-dimensional hydraulic fracture simulation experimental device comprises a confining pressure chamber, a pressurization device and a control portion; the confining pressure chamber has a rectangular cross section, and a top portion of the confining pressure chamber is hermetically provided with an upper cover which is dismountable and provided with a sealed transparent window; the confining pressure chamber is further provided with a through and sealable vent hole that can be communicated with a vacuum pump or a pore pressure pump;
    the pressurization device comprises a lateral pressurization plate provided in the confining pressure chamber and capable of applying a horizontal pressure to the rock sample; the lateral pressurization plate is connected with a lateral pressurization hydraulic structure capable of driving the lateral pressurization plate to move horizontally and applying a horizontal pressure; one sidewall of the confining pressure chamber is set as a first sidewall, and the other sidewall adjacent to the first sidewall is set as a second sidewall; the lateral pressurization plate comprises a first lateral pressurization plate provided in parallel with the first sidewall, and a second lateral pressurization plate provided in parallel with the second sidewall; the lateral pressurization hydraulic structure comprises a first lateral pressurization hydraulic cylinder provided on an outer wall of the first sidewall and capable of driving the first lateral pressurization plate to move horizontally in a lengthwise direction of the second sidewall; the lateral pressurization hydraulic structure further comprises a second lateral pressurization hydraulic cylinder provided on an outer wall of the second sidewall and capable of driving the second lateral pressurization plate to move horizontally in a lengthwise direction of the first sidewall; both the first lateral pressurization hydraulic cylinder and the second lateral pressurization hydraulic cylinder are provided to be in communication with a confining pressure pump; the pressurization device further comprises a longitudinal pressurization plate hermetically provided at a bottom portion of the confining pressure chamber and capable of applying a vertical pressure to the rock sample; a bottom portion of the longitudinal pressurization plate is detachably connected with a longitudinal pressurization hydraulic cylinder capable of driving the longitudinal pressurization plate to move up and down and applying a vertical pressure; the longitudinal pressurization plate is provided with a plurality of fluid injection holes and a plurality of pressure measuring holes, each of the fluid injection holes is provided to be in communication with a fracturing fluid injection pump;
    the control portion comprises a data collection unit and a control unit, wherein the data collection unit comprises the high-speed camera suspended above the upper cover and a pressure probe provided in each of the pressure measuring holes; the control unit is configured to receive image information and pressure information transmitted by the data collection unit, and capable of controlling work states of the fracturing fluid injection pump, the lateral pressurization hydraulic structure, and the longitudinal pressurization hydraulic cylinder.

4. The visualized supercritical carbon dioxide fracturing physical simulation test method according to claim 3, wherein in step c, it is set that the vertical pressure applied to the rock sample by the longitudinal pressurization hydraulic cylinder is a Z-direction compressive stress, the horizontal pressure applied to the rock sample by the second lateral pressurization hydraulic cylinder is an X-direction horizontal compressive stress, the horizontal pressure applied to the rock sample by the first lateral pressurization hydraulic cylinder is a Y-direction horizontal compressive stress, and the prefabricated fracture is provided in the lengthwise direction of the first sidewall, wherein the X-direction horizontal compressive stress is greater than the Y-direction horizontal compressive stress; the Z-direction compressive stress, the X-direction horizontal compressive stress, and the Y-direction horizontal compressive stress constitute the three-way confining pressure of the rock sample.

5. The visualized supercritical carbon dioxide fracturing physical simulation test method according to claim 3, wherein in step c, the vent hole in the confining pressure chamber is in communication with the pore pressure pump, and the pore pressure pump injects liquid into the confining pressure chamber, so that the rock sample is sufficiently saturated and reaches a preset pore pressure.

6. The visualized supercritical carbon dioxide fracturing physical simulation test method according to claim 3, wherein in step d, the supercritical carbon dioxide fracturing fluid is injected into the confining pressure chamber via the fracturing fluid injection pump, with an injection rate of 5 ml/min to 25 ml/min.

7. The visualized supercritical carbon dioxide fracturing physical simulation test method according to claim 1, wherein in step d, a temperature of the supercritical carbon dioxide fracturing fluid is above 32° C.

8. The visualized supercritical carbon dioxide fracturing physical simulation test method according to claim 1, wherein in step d, when the fluid injection pressure of the supercritical carbon dioxide fracturing fluid is decreased to be 20% of a peak pressure, the fluid injection is stopped.

* * * * *